United States Patent [19]

Anderson et al.

[11] 4,072,154

[45] Feb. 7, 1978

[54] SEALING ARRANGEMENT FOR HEART PACER ELECTRODE LEADS

[75] Inventors: Jon A. Anderson, New Brighton; Wendell R. Malin, Edina, both of Minn.

[73] Assignee: Cardiac Pacemakers, Inc., St. Paul, Minn.

[21] Appl. No.: 691,032

[22] Filed: May 28, 1976

[51] Int. Cl.² ............................................. A61N 1/36
[52] U.S. Cl. ............................... 128/419 P; 277/177; 339/94 C
[58] Field of Search ............. 128/418, 419 P, 419 PG, 128/421, 422, 423; 339/60 R, 60 C, 94 R, 94 C; 277/183 A, 177

[56] References Cited
U.S. PATENT DOCUMENTS

| 3,582,094 | 6/1971 | Whittaker | 277/177 X |
| 3,760,332 | 9/1973 | Berkovits et al. | 128/419 P X |
| 3,842,387 | 10/1974 | Santangello | 339/94 R X |
| 3,924,639 | 12/1975 | Hess | 128/419 P |

Primary Examiner—William E. Kamm
Attorney, Agent, or Firm—Orrin M. Haugen; Thomas J. Nikolai

[57] ABSTRACT

An improved electrode sealing arrangement for use on lead assemblies to be coupled to an implantable pulse generator to form a cardiac pacer apparatus. The conductive portion of the lead includes a terminal pin which is both rigid and durable, and which is arranged to be clamped between a set screw and a terminal post. The improved sealing means includes a generally closed cylindrical resilient segment which is arranged generally coaxially of the lead conductor, with a resilient peripheral sleeve extending outwardly of the cylindrical segment and having a raised resilient ring extending continuously about the outer periphery of the peripheral sleeve. The raised resilient ring is disposed axially outwardly from the distal end of the terminal pin, so as to provide an axial displacement between the terminal pin and the resilient sealing ring. Since the peripheral seal arrangement permits substantial canting and deflection of the lead assembly within the tubular bore formed in the pulse generator without adversely affecting the sealing conditions, ease of lead insertion is facilitated due to the increased tolerances which may be employed between the inner end of the lead and the pulse generator connector block.

1 Claim, 4 Drawing Figures

SEALING ARRANGEMENT FOR HEART PACER ELECTRODE LEADS

BACKGROUND OF THE INVENTION

The present invention relates generally to an improved lead assembly for use in combination with an implantable pulse generator to form a cardiac pacer apparatus, and more specifically to a system for sealing the lead assemblies into place in the implantable pulse generator so as to accommodate ease of assembly during implant and to resist during the extended implant period, any influx of body fluids which could interfere with normal operation of the pulse generator, and thereby detract from the efficiency of the pacer apparatus.

Cardiac pacers are employed at the present time to treat various problems in the heart, including treatment of arrhythmias or other disorders which require external stimulation to sustain adequate cardiac output. Cardiac pacers in use today include asynchronous units as well as demand-inhibit units, with the selection being indicated by the patient's condition.

Artificial electronic pacers very nearly approximate the electrical impulses normally delivered by the natural cardiac conduction network. These electronic pacers consist of a pulse generator and an insulated conductive wire lead, the pacer emitting small, sequentially timed electrical impulses which cause the ventricular heart muscles to contract. In a normal person, ventricular contractions result from depolarization caused by transmission of signals from the sino-atrial node through the atrial-ventricular node and the Common Bundle (His) to the right and left bundle branches and the Purkinje Network. When a segment of this natural conduction system becomes blocked, such as when there is no conduction through the Bundle of His, an artificial pacer is normally required to maintain an adequate and appropriate heart rate and rhythm.

In an implantable cardiac pacer assembly or system, the combination of a pulse generator and lead is employed, the term "pulse generator" normally refers to the implantable electronic device, while the term "lead" refers to the insulated conductive wire which is electrically and mechanically coupled to the pulse generator and which receives the stimulating impulse from the pulse generator and transmits this impulse to the heart. The lead incorporates an electrode which is the conductive element or contact, normally exposed, on or adjacent the distal end of the lead to establish electrical contact with the heart muscle.

In an implantable system, either endocardial leads or myocardial leads may be employed. Endocardial leads are those leads which enter the heart through a vein and make contact with the endocardium, while myocardial leads are those which are attached to the surface of the heart with an electrode making contact with the myocardium.

Established procedures are employed for the lead placement, with these procedures being well known in the art. Following placement of the lead, electrode thresholds are determined and upon an indication of satisfactory thresholds, the proximal ends of the leads are connected to the pulse generator. This connection is normally accomplished by the insertion of the exposed terminal pin of the lead into the connector block of the pulse generator. Inasmuch as the terminal pin and the connector block have exposed conductive surfaces, it is essential that the zone surrounding the terminal pin-connector block assembly be sealed and maintained free of body fluids. Leakage of body fluids into the cavity or zone occupied by the terminal pin-connector block combination may adversely affect pacer performance, hence durable seals must be provided.

The procedure for inserting the leads into the pulse generator must be one which can be accomplished with a maximum degree of freedom, so as to avoid inadvertent moving of the placed electrode and lead. This requires, in turn, that the insertion of the terminal pin into the connector block be accomplished with ease. Regrettably, as one attempts to facilitate ease of insertion of the terminal pin into the connector block, one further complicates or interferes with normal sealing between the proximal end of the lead and the pulse generator. In accordance with the present invention, however, an improved sealing arrangement is provided which enables ease of insertion of the terminal pin into the connector block, without adversely affecting the quality of the seal.

In order to improve the quality of the seal and for mechanical integrity, the terminal pin extends axially into that portion of the lead which is received within the body of the pulse generator. The terminal pin, which is durable and rigid, preferably terminates at a point axially spaced inwardly from the zone of the seal. Therefore, the rigid pin may be accommodated within a bore formed in the connector block, with the bore formed in the connector block being of a radial dimension sufficiently great so as to readily receive and accommodate the exposed portion or segment of the terminal pin. Thereafter, when the set screw is forced against the surface of the exposed portion of the terminal pin, any radial deflection of the terminal pin may be accommodated without adversely affecting or destroying the seal established between the lead and the lead accommodating bore formed in the pulse generator.

SUMMARY OF THE INVENTION

Briefly, in accordance with the present invention, the proximal end of the lead is provided with a generally closed cylindrical resilient segment which terminates adjacent the exposed terminal pin, with the cylindrical resilient segment being further provided with a resilient peripheral sleeve extending outwardly of the cylindrical segment and with a raised resilient ring extending continuously about the outer periphery of the peripheral sleeve. This sealing arrangement is preferably disposed at a point remote from the terminal pin in order to provide a flexible transition which is as smooth as possible under the circumstances. The flexible transition is further accommodated by disposing or placing the inner end of the terminal pin at a point spaced from the outer peripheral seal. The flexible transition must have a finite dimension in order to improve the operational features of the structure. The physical configuration of the seal permits, therefore, both deflection and canting of the cylindrical segment of the lead containing the rigid terminal pin without adversely affecting the sealing characteristics of the seal system.

Therefore, it is a primary object of the present invention to provide an improved seal arrangement for a lead assembly used in combination with an implantable pulse generator to form a cardiac pacer system.

It is a further object of the present invention to provide an improved seal arrangement for a lead assembly utilized in combination with an implantable pulse generator of a cardiac pacer system, and wherein the seal arrangement effectively isolates the mated connector block-terminal pin combination, while facilitating ease of assembly of the terminal pin within the connector block arrangement.

It is yet a further object of the present invention to provide an improved sealing arrangement for a lead assembly used in combination with an implantable pulse generator forming a cardiac pacer system, and wherein modest misalignments between the lead assembly and the lead assembly receiver of the pulse generator may be accommodated without adversely affecting the sealing surface therebetween.

Other and further objects of the present invention will become apparent to those skilled in the art upon a study of the following specification, appended claims, and accompanying drawing.

DESCRIPTION OF THE PREFERRED EMBODIMENT

Figure 2:
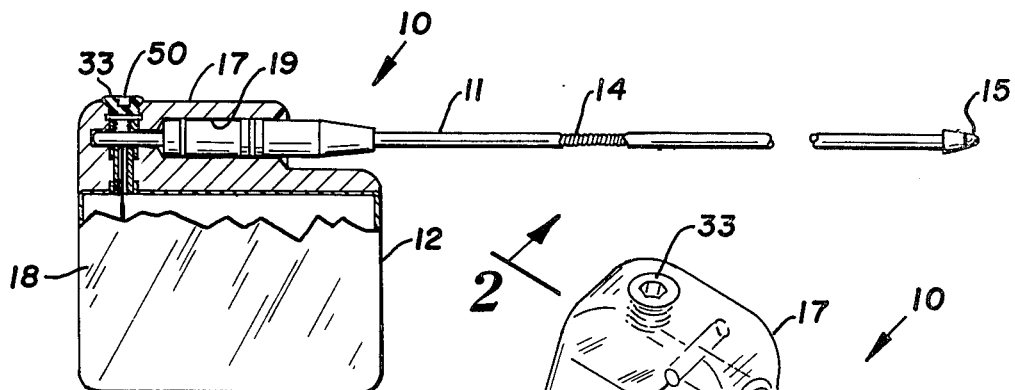
FIG. 2 is a side elevational view, partially in section, and illustrating the pulse generator-lead assembly combination shown in FIG. 1, with the lead assembly being fragmented in order to show the electrode at the distal end thereof, and with the sectional portion of FIG. 2 being taken along the line and in the direction of the arrows 2—2 of FIG. 1.
Figure 1:
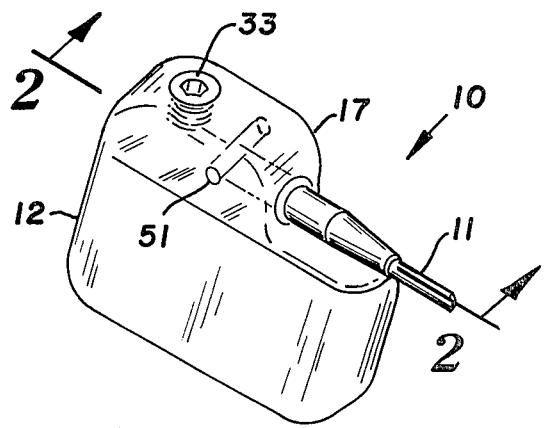
FIG. 1 is a perspective view of an implantable pulse generator having a lead assembly coupled thereto, with a portion of the lead assembly being broken away.

In accordance with the preferred embodiment of the present invention, and with particular attention being directed to FIGS. 1 and 2 of the drawing, it will be seen that the cardiac pacer apparatus or system generally designated 10 includes lead assembly 11 along with pulse generator 12. As is apparent from FIG. 2, the lead assembly 11 consists of an elongated generally tubular structure having a conductive element disposed therewithin, such as is illustrated in the broken away zone at 14, and with an electrode 15 at the tip of the cone being coupled to the conductive element and disposed at the distal end of the lead assembly. The lead assembly 11 may be constructed in accordance with the lead assembly disclosed in, the David Charles Amundson U.S. Pat. No. 4,033,355; and assigned to the same assignee as the present invention.

As is apparent, a transparent epoxy member 17 is coupled to the enclosure 18 of the pulse generator 12, with epoxy member 17 having a bore 19 formed therewithin to receive the proximal end of lead assembly 11. With attention being directed to FIG. 3 of the drawing, the proximal end of lead assembly 11 includes a generally closed cylindrical resilient segment 20 arranged generally coaxially of conducting element 14, with the conductive element 14 terminating in terminal pin 22. Sealing means are provided about the periphery of cylindrical segment 20, as at 23 and 24, with the latter sealing means being described more fully hereinafter.

Figure 4:
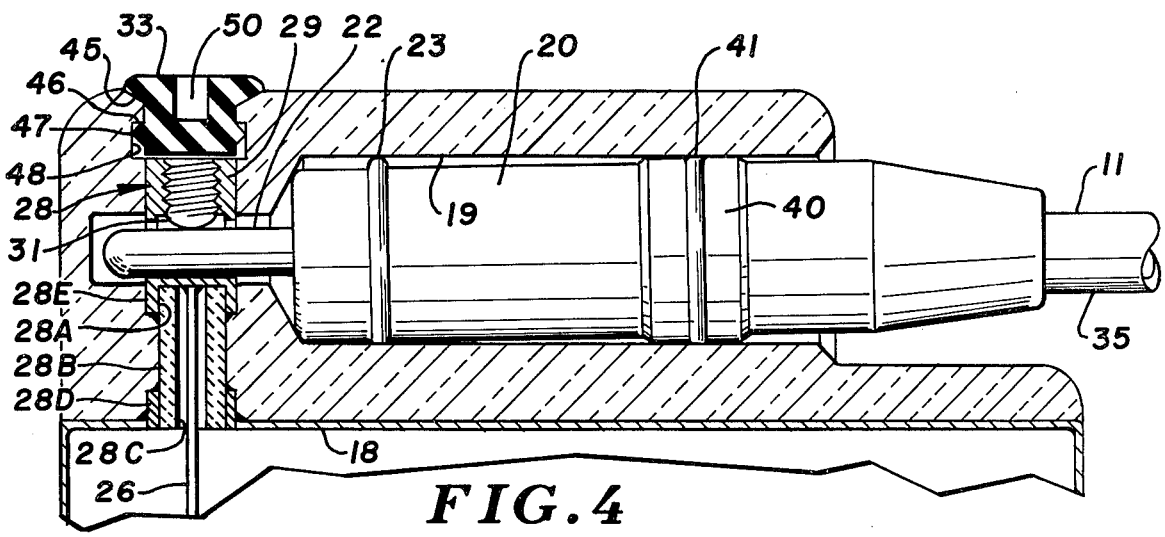
FIG. 4 is a view similar to FIG. 3, and illustrating the structure with the terminal pin of the lead assembly firmly engaged by the connector block of the pulse generator, and illustrating, in slightly exaggerated form, the misalignment or canting which occurs between the proximal end of the lead assembly and the lead assembly receiver, and further illustrating the effective seal existing between the periphery of the lead assembly and the bore of the pulse generator.

Pulse generator 12 is provided with an output lead member 26 which is arranged to pass through a seal member, and ultimately make contact with connector block generally designated 28. Connector block 28 includes a base or anvil member 29 having an upper tapped portion 30 with a set screw 31 threadably received therewithin. Set screw 31 is arranged to be screwed inwardly in member 30 and ultimately engage for mechanical and electrical purposes, the shank of terminal pin 22 at a point adjacent the free end particularly as is indicated in FIG. 4. Connector block 28 is provided with a bore adjacent the base end thereof, such as at 28A, with this bore being arranged to accommodate ceramic sleeve member or insulator 28B therewithin. The ceramic sleeve 28B has an internal bore as at 28C to receive and accommodate output lead member 26, as indicated. A metal sleeve member 28D is bonded hermetically about the outer periphery of ceramic sleeve 28B, and may be brazed and thereby sealed to the metallic enclosure 18, as illustrated. In order to complete the assembly, a second sleeve element as at 28E is provided adjacent the upper end of the sleeve so as to provide a means for securing connector block 28 to ceramic sleeve 28B. Plug seal 33 is provided for closing bore or opening 34 in the epoxy member 17, with plug 33 being a resilient member having dimensions selected so as to effectively seal opening 34.

Figure 3:
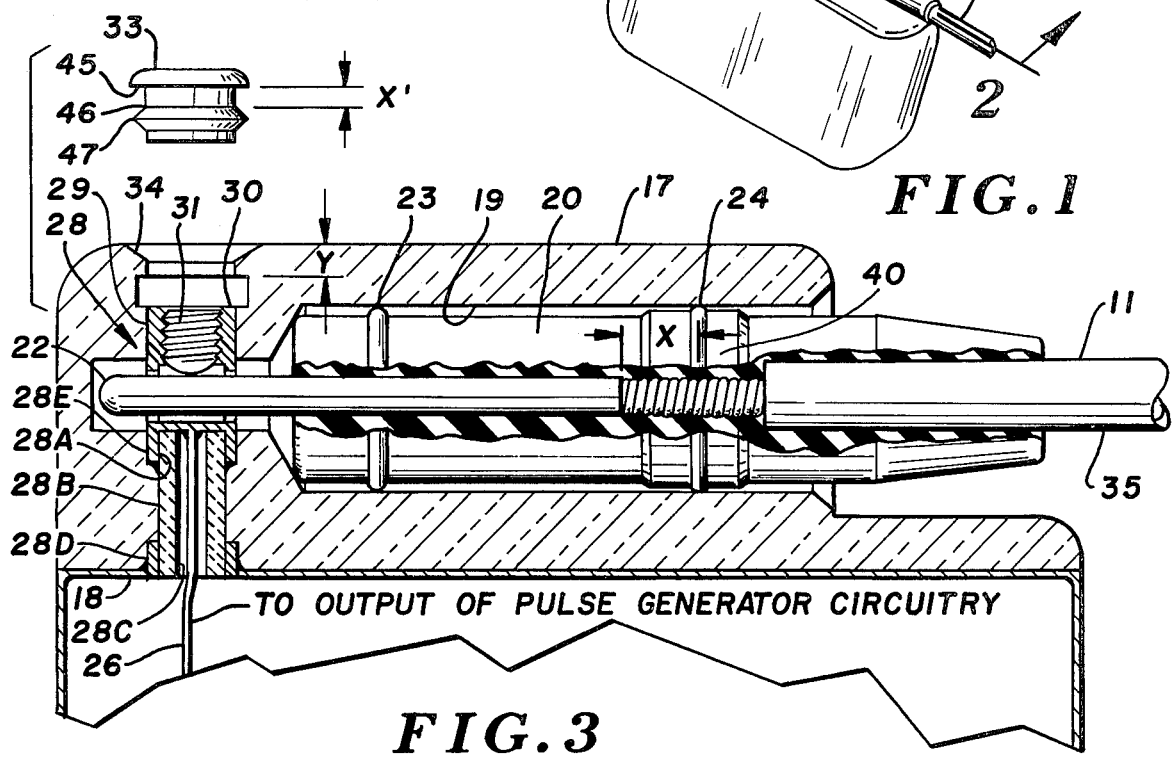
FIG. 3 is a partial vertical sectional view on a slightly enlarged scale, and illustrating the manner in which the lead assembly is received within the bore formed in the pulse generator body, and illustrating the plug seal component in exploded disposition relative to the pulse generator.

With continued attention being directed to FIGS. 3 and 4, it will be observed that cylindrical segment 20, which is bonded or otherwise secured to the tubing element 35 of lead assembly 11 has seals 23 and 24 arranged about the periphery thereof. Seal 23 is in the form of a radially outwardly extending member having a semi-circular cross-section, thereby presenting an outer configuration similar to the outer portion of an "O"-ring. Seal 24 is significantly different from seal 23.

Seal 24 is provided with a resilient peripheral sleeve segment 40 which extends outwardly of the periphery of cylindrical segment 20, and is provided with a raised resilient ring or sleeve member which extends continuously about the outer periphery of cylindrical segment 20. A raised resilient ring 41 extends continuously about the outer periphery of sleeve 40, with the outer portion of ring 41 having a cross-section generally that of a semi-circle, and being integrally molded generally diametrically to the outer surface of peripheral sleeve 40. The outer diameter of members 23 and 41 are generally approximately 0.20 mm greater than the inner diameter of bore 19, thereby providing a substantial interference fit and thereby accomplishing sealing. The utilization of the raised sleeve 40 provides axial support for ring 41, and thereby enhances or preserves the sealing capability of ring 41 in spite of modest axial misalignment and deflection between cylindrical segment 20 and the cylindrical segment receiving bore 19 formed in epoxy member 17 of pulse generator 12. It will be observed that epoxy member 17 is transparent, thereby enabling the visual determination of the position of terminal pin 22 relative to connector block 28. This is, of course, helpful during assembly of the pulse generator to the lead assembly after placement of the lead assembly within the patient.

In addition to the sealing surfaces provided by members 23 and 41, it will be observed that the base end of cylindrical segment 20 seals against the tapered portion of bore 19. Therefore, three serially arranged seals are provided, all of which contribute to affecting a proper and effective seal for the lead assembly as it enters the pulse generator.

As is apparent in FIG. 3, terminal pin 22 extends inwardly of cylindrical segment 20, and terminates, where indicated, at a point spaced from the center of seal 24 by a dimension "X". It is this dimensional arrangement which accommodates radial deflection of the pin 22 relative to the cylindrical segment 20, thereby facilitating a seal when the set screw 31 is locked against the terminal pin 22.

Typically, in a lead assembly having a cylindrical segment 20 with a diameter of 5.6 mm, the magnitude of dimension "X" is typically 2 mm. Workable dimensions would, of course, be somewhat broader, such as in the range of from 1 to 5 mm.

The physical configuration of plug seal 33 is selected so as to enhance the sealing achieved. Sealing surfaces are provided as at 45, 46, and 47. The outer diameter of plug seal 33 as at 47 is greater than the inner diameter of bore 48, thereby effecting a seal. Furthermore, in this connection, the dimension "X'" illustrated in plug seal of FIG. 3 is less than the corresponding dimension "Y" in the opening formed in the epoxy member 17 of pulse generator 12. Therefore, by pre-selecting these dimensions as described, a sealing surface is generated as at 45 and also 46 between the plug seal 33 and epoxy member 17.

In order to provide for the smooth transition between sealing member or surface 41 and the inner surface of bore 19, the axial spacing between terminal pin 22 and sealing surface 41 should be as great as reasonably possible. Therefore, any misalignment or canting between the lead assembly and the bore formed in the pulse generator may be accommodated, with this accommodation being obtained without sacrificing the quality of the seal formed between the lead assembly and the pulse generator.

By way of actual procedure, after the electrode has been satisfactorily placed in situ with proper electrical thresholds determined, and the pocket for the pulse generator has been prepared in the usual way, the leads are then arranged to be connected to the pulse generator. Initially, the external surface of cylindrical segment 20 is coated with a film of sterile mineral oil. The proximal end of the lead assembly including the terminal pin and cylindrical segment 20 are inserted into bore 19, with insertion continuing until terminal pin 22 is visibly within and properly sealed in connector block 28. Set screw 31 is then tightened with an Allen wrench with insertion pressure continuing to be applied between the proximal end of the lead assembly 11 and pulse generator 12 such as the shank portion of terminal pin 22. The continued application of insertion pressure assists in effecting the seal, and the application of firm forces between set screw 31 and terminal pin 22 provide a reliable electrical connection between the surfaces of set screw 31 and terminal pin 22. The plug seal member 33 is then coated with medical adhesive, if desired, or merely inserted into the opening 34 with the tip of the Allen wrench, bore or opening 50 in plug 33 being formed to receive an Allen wrench therewithin. A suture hole is illustrated as at 51, and is provided for securing the pulse generator in the pocket to prevent undesired migration of the assembly.

By way of materials of construction, enclosure 18 of pulse generator 12 is preferably fabricated from stainless steel, with epoxy cap member 17 being, of course, prepared from thermosetting epoxy resins suited for implant purposes. Leads such as lead 11 are formed of conductive elements such as elements 14 together with silicone rubber tubular sleeves. Furthermore, conductor 15 is formed with a hollow core therewithin in order to permit the lead assembly to receive an internal stylet for use as a placement aid. Additional details of the structure of typical electrode lead assemblies are given in the David Charles Amundson U.S. Pat. No. 4,033,355, entitled "ELECTRODE LEAD ASSEMBLY FOR IMPLANTABLE DEVICES" and assigned to the same assignee as the present invention.

While the apparatus illustrated in the specific embodiment herein is a unipolar device, it will be appreciated that the lead assembly and sealing arrangement illustrated will be equally suited for bipolar structures. Also, the specific mode of operation of the pulse generator is not critical to the functionality of the lead assembly, and hence the lead assembly illustrated may be utilized in combination with any type of implantable pulse generator. A typical example of circuitry for use in such a pulse generator is illustrated in, the Jon A. Anderson, et al U.S. Pat. No. 4,041,953, entitled "CARDIAC PACER CIRCUIT", and assigned to the same assignee as the present invention.

We claim:

1. In combination, a lead assembly and an implantable pulse generator forming a cardiac pacer apparatus:
   a. said lead assembly comprising an elongated generally tubular lead having a conductive element disposed therewithin, with electrode means coupled to said conductive element and disposed at the distal end of said lead assembly, and electrical and mechanical connector means at the proximate end thereof for coupling said lead assembly to said pulse generator;
   b. said pulse generator comprising an enclosure having a bore formed therewithin for receiving said connector means in sealed relationship within said bore, connector block means disposed within said bore for securing the proximal end of said conductive element to said pulse generator and sealing means disposed about the periphery of said lead assembly at a point adjacent said proximal end and normally disposed within said bore when said lead is coupled to said connector means;
   c. said sealing means including a generally closed cylindrical resilient segment arranged generally coaxially of said conductive element with a resilient peripheral sleeve extending outwardly of said cylindrical segment and with a first raised resilient ring disposed about the periphery of said cylindrical segment and disposed between the base of said cylindrical segment at the proximal end thereof and the proximal end of said peripheral sleeve and with a second raised resilient ring extending continuously about the outer periphery of said peripheral sleeve, said resilient peripheral sleeve having axially extending portions arranged in oppositely disposed relationship of said second raised resilient ring; and
   d. a rigid terminal pin member disposed generally coaxially thereof, with one end of said pin being lockingly received within a bore formed in said connector block means and with the other end of said rigid terminal pin being spaced axially inwardly of said resilient peripheral sleeve and outwardly of said first raised resilient ring.

* * * * *